(12) United States Patent
Okamura et al.

(10) Patent No.: US 9,568,598 B2
(45) Date of Patent: Feb. 14, 2017

(54) ULTRASONIC DIAGNOSTIC APPARATUS AND PROGRAM

(75) Inventors: Yoko Okamura, Nasushiobara (JP); Naohisa Kamiyama, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1234 days.

(21) Appl. No.: 12/484,465

(22) Filed: Jun. 15, 2009

(65) Prior Publication Data

US 2009/0318809 A1 Dec. 24, 2009

(30) Foreign Application Priority Data

Jun. 18, 2008 (JP) .................. 2008-159560

(51) Int. Cl.
*G01S 7/52* (2006.01)
*A61B 8/14* (2006.01)
*A61B 8/00* (2006.01)
*A61B 8/08* (2006.01)
*G01S 15/89* (2006.01)

(52) U.S. Cl.
CPC ............ *G01S 7/52077* (2013.01); *A61B 8/14* (2013.01); *A61B 8/463* (2013.01); *A61B 8/488* (2013.01); *A61B 8/5238* (2013.01); *G01S 7/52073* (2013.01); *G01S 15/8918* (2013.01)

(58) Field of Classification Search
CPC ........... A61B 8/14; A61B 8/463; A61B 8/488; A61B 8/5238; G01S 15/8918; G01S 7/52073; G01S 7/52077
USPC .......................... 600/407, 437, 443; 382/128
See application file for complete search history.

(56) References Cited

U.S. PATENT DOCUMENTS

2006/0241431 A1  10/2006  Kamiyama
2008/0319317 A1  12/2008  Kamiyama et al.

FOREIGN PATENT DOCUMENTS

| EP | 1 982 654 A1 | 10/2008 |
| JP | 2003-61964 A | 3/2003 |
| JP | 2007-313114 | 12/2007 |
| WO | WO 00/20887 | 4/2000 |
| WO | WO 2007/114375 A1 | 10/2007 |

OTHER PUBLICATIONS

English translation of JP 2003-061964 (Naohisa) provided by IPDL.*

(Continued)

*Primary Examiner* — Katherine Fernandez
(74) *Attorney, Agent, or Firm* — Oblon, McClelland, Maier & Neustadt, L.L.P.

(57) ABSTRACT

An ultrasonic diagnostic apparatus comprises an ultrasonic probe configured to transmit ultrasound to a test body and receive an echo signal, an image generation unit configured to generate a plurality of tomograms with respect to the test body based on the echo signal, an image memory configured to record the generated tomograms, and a control processor. The control processor performs control such that image processing of extracting a microstructure is performed, using correlation between a tomogram stored in the image memory and a tomogram corresponding to a position of the ultrasonic probe at that point in time. The microstructure-extracted image is displayed on the display part in a predetermined form.

7 Claims, 8 Drawing Sheets

(56) References Cited

OTHER PUBLICATIONS

Jafar Saniie, et al., "Analysis of Order-Statistic CFAR Threshold Estimators for improved Ultrasonic Flaw Detection", IEEE Transactions on Ultrasonics, Ferroelectrics, and Frequency Control, vol. 39, No. 5, Sep. 1992, pp. 618-630.
Office Action issued Nov. 13, 2012 in Japanese Patent Application No. 2008-159560 (with English-language translation).
Japanese Office Action with English translation mailed Feb. 5, 2013, in Japanese Patent Application No. 2008-159560, filed Jun. 18, 2008.

* cited by examiner

ULTRASONIC DIAGNOSTIC APPARATUS AND PROGRAM

CROSS-REFERENCE TO RELATED APPLICATIONS

This application is based upon and claims the benefit of priority from prior Japanese Patent Application No. 2008-159560, filed Jun. 18, 2008, the entire contents of which are incorporated herein by reference.

BACKGROUND OF THE INVENTION

1. Field of the Invention

The present invention relates to an ultrasonic diagnostic apparatus and program for extracting and displaying a minute structure in a living body organ from an echo signal of tissue.

2. Description of the Related Art

In ultrasonic diagnosis, heart beats and fetal movements can be displayed in real time through a simple operation of placing an ultrasonic probe over the surface of a body. Since ultrasonic diagnosis has a high level of safety, ultrasonic diagnostic tests can be performed repeatedly. Further, an ultrasonic diagnostic apparatus is smaller than other diagnostic apparatuses employing X-rays, CT, and MRI, for example. Thus, ultrasonic diagnosis is a simple and easy diagnostic scheme, allowing the ultrasonic diagnostic apparatus to be easily moved to the bedside for diagnosis, for example.

Ultrasonic diagnostic apparatuses vary greatly depending on the kind of functions equipped therein. Among compact types, ultrasonic diagnostic apparatuses which can be carried with one hand have been developed. Unlike the use of X-rays, for example, ultrasonic diagnosis is free from the influence of exposure to radiation, and can be used in obstetrics or home medical care, for example.

One of ultrasonic diagnoses offering various advantages as described above is early diagnosis for breast cancer. It is known that microcalcifications occur in breast tissue with a high frequency as a sign of breast cancer. One or more microcalcification lesions are topically scattered. Since calcium is higher in hardness than body tissue, calcium reflects ultrasound well. Microcalcification lesions should therefore have high brightness on an image. In actuality, however, when an image is observed by the eye, it is said that microcalcification lesions even with the size of approximately several hundred microns are difficult to be detected.

On an ultrasonic image, interference fringes called a speckle pattern, which is caused by random interference of ultrasound, may occur. A speckle pattern is used for diagnosis of cirrhosis.

A speckle pattern closely resembles microstructures which are often overlooked in a diagnosis for breast cancer, and can be confusing image information for diagnosis in some cases. Thus, in a diagnosis for breast cancer, there is a need for removal of a speckle pattern.

In view of the above-described circumstances, techniques such as spatial compounding, a constant false alarm rate (CFAR) process, and similarity filtering. The spatial compounding is a process of superimposing transmission and reception signals from different directions and smoothing speckles. The CFAR process is a process of subtracting a neighboring average of brightness from the target pixel, and uses the subtracted result to extract high-brightness portions. The similarity filtering is a process of removing speckles using its statistical properties. As well as the above-described techniques for removal of speckle patterns, in fields other than the ultrasonic diagnosis, various attempts to automatically recognize microcalcifications have been reported mainly as applications of X-ray diagnosis images.

The mammary gland, which is a target of a diagnosis, has a complex structure especially in the lactiferous duct, for example, and is not a homogenous organ in nature. Thus, according to the conventional filtering process, upon detection of microcalcifications, the mammary gland structure is also extracted as a structure, and the two cannot be distinguished sufficiently.

Since structures such as the lactiferous duct are clearly larger than microcalcifications, the two can sometimes be distinguished by the eye even if the lactiferous duct remains after the filtering process. However, the inventors have often experienced difficulties in making such a distinction in research. In particular, when only a part of the mammary gland structure remains, the remaining mammary gland structure may look similar to microcalcifications, since the mammary gland structure is shown as dots on an image after the filtering process.

Furthermore, a speckle pattern on an image may vary randomly. In such a case, even after performing a predetermined speckle reduction process, speckles remain, which makes it difficult to distinguish between the remaining speckles and calcified parts.

In view of such circumstances, Japanese Patent KOKAI Publication No. 2007-313114 discloses the following technique. That is, Japanese Patent KOKAI Publication No. 2007-313114 discloses an ultrasonic diagnostic apparatus for image processing of extracting a microstructure using a first ultrasonic image and a second ultrasonic image determined based on the position of the first ultrasonic image, comprising an image processing means for generating a microstructure-extracted image by performing a microstructure extraction process of calculating a difference from a maximum pixel value of a reference region in the second ultrasonic image including a spatially corresponding pixel, with respect to each pixel in the first ultrasonic image, and display means for displaying the microstructure-extracted image in a predetermined form.

According to the ultrasonic diagnostic apparatus disclosed in Japanese Patent KOKAI Publication No. 2007-313114, by using spatial three-dimensional information instead of a slice of a tomogram in signal processing, continuous structures such as the mammary gland and microstructures such as microcalcified parts are accurately distinguished, and the microstructures can be extracted.

An ultrasonic probe used in the technique disclosed in Japanese Patent KOKAI Publication No. 2007-313114 is capable of ultrasonically scanning a three-dimensional region of a test body. Accordingly, ultrasonic probes used in the technique disclosed in Japanese Patent KOKAI Publication No. 2007-313114 include an ultrasonic probe (referred to as a mechanical 4D ultrasonic probe) with a configuration in which a vibrator mechanically vibrates in an orthogonal direction of its arranging direction and a three-dimensional region is ultrasonically scanned, and an ultrasonic probe (referred to as a real-time 3D ultrasonic probe) with a configuration in which a three-dimensional region is ultrasonically scanned by electric control using two-dimensional vibration elements arranged two-dimensionally.

In the mechanical 4D ultrasonic probe, the test body is three-dimensionally scanned by the vibrator circuit. The tester can therefore automatically acquire a plurality of two-dimensional tomograms only by making the main body of the ultrasonic probe contact the test body. Further, an accurate distance between the cross-sections can also be detected from the controlled vibration rate. In the real-time 3D ultrasonic probe, on the other hand, a three-dimensional region can be ultrasonically scanned in principle in a time same as that required for acquiring the conventional two-dimensional tomograms.

Because of the size and weight, however, the mechanical 4D ultrasonic probe has problems of difficulty in scanning for capturing a minute structure and insufficiency in real-time properties. Further, the real-time 3D ultrasonic probe conceivably requires further time for development.

Accordingly, under the present circumstances, a technique by which a diagnosis result of a clinically permissible level (at which a microstructure can be extracted), using a conventional 1D ultrasonic probe (including a 1.5D ultrasonic probe) as an ultrasonic probe, is strongly desired. In other words, a technique by which a desired microstructure-extracted image can be obtained in real time using a 1D ultrasonic probe, which is the most common ultrasonic probe, is desired.

BRIEF SUMMARY OF THE INVENTION

An object of the present invention, which was made in consideration of the above-described circumstances, is to provide an ultrasonic diagnostic apparatus and program for accurately distinguishing between continuous structures such as the mammary gland and microstructures such as microcalcified parts, and acquiring a desired microstructure-extracted image in real time, using a conventional 1D ultrasonic probe as the ultrasonic probe.

In order to achieve the above-described object, an ultrasonic diagnostic apparatus according to a first embodiment of the present invention is an ultrasonic diagnostic apparatus configured to ultrasonically scan a test body and acquire a tomogram, comprising:

an ultrasonic probe configured to transmit ultrasound to the test body and receive an echo signal from the test body;

an image generation part configured to generate a plurality of tomograms with respect to the test body based on the echo signal received by the ultrasonic probe;

a storage part configured to store the tomogram generated by the image generation part;

an image processing part configured to perform image processing of extracting a microstructure using correlation between the tomogram stored in the storage part and a tomogram corresponding to a position of the ultrasonic probe at that point in time; and a display part configured to display the microstructure-extracted image generated by the image processing part in a predetermined form.

In order to achieve the above-described object, a program according to the second embodiment of the present invention is a program of functionalizing a computer as an ultrasonic diagnostic apparatus configured to ultrasonically scan a test body and acquire a tomogram, wherein functions which the program causes the computer to implement include:

a function of causing an ultrasonic probe to transmit ultrasound to the test body and receive an echo signal from the test body;

an image generation function of generating a plurality of tomograms regarding the test body based on the echo signal;

a storage function of storing the tomograms;

an image processing function of performing image processing of extracting a microstructure using correlation between a tomogram stored using the storage function and a tomogram corresponding to a position of the tomogram at that point in time, and generating a microstructure-extracted image; and a display function of displaying the microstructure-extracted image in a predetermined form.

According to the present invention, it is possible to provide an ultrasonic diagnostic apparatus and program for accurately distinguishing between continuous structures such as the mammary gland and microstructures such as microcalcified parts, and acquiring a desired microstructure-extracted image in real time, using a conventional 1D ultrasonic probe as the ultrasonic probe.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
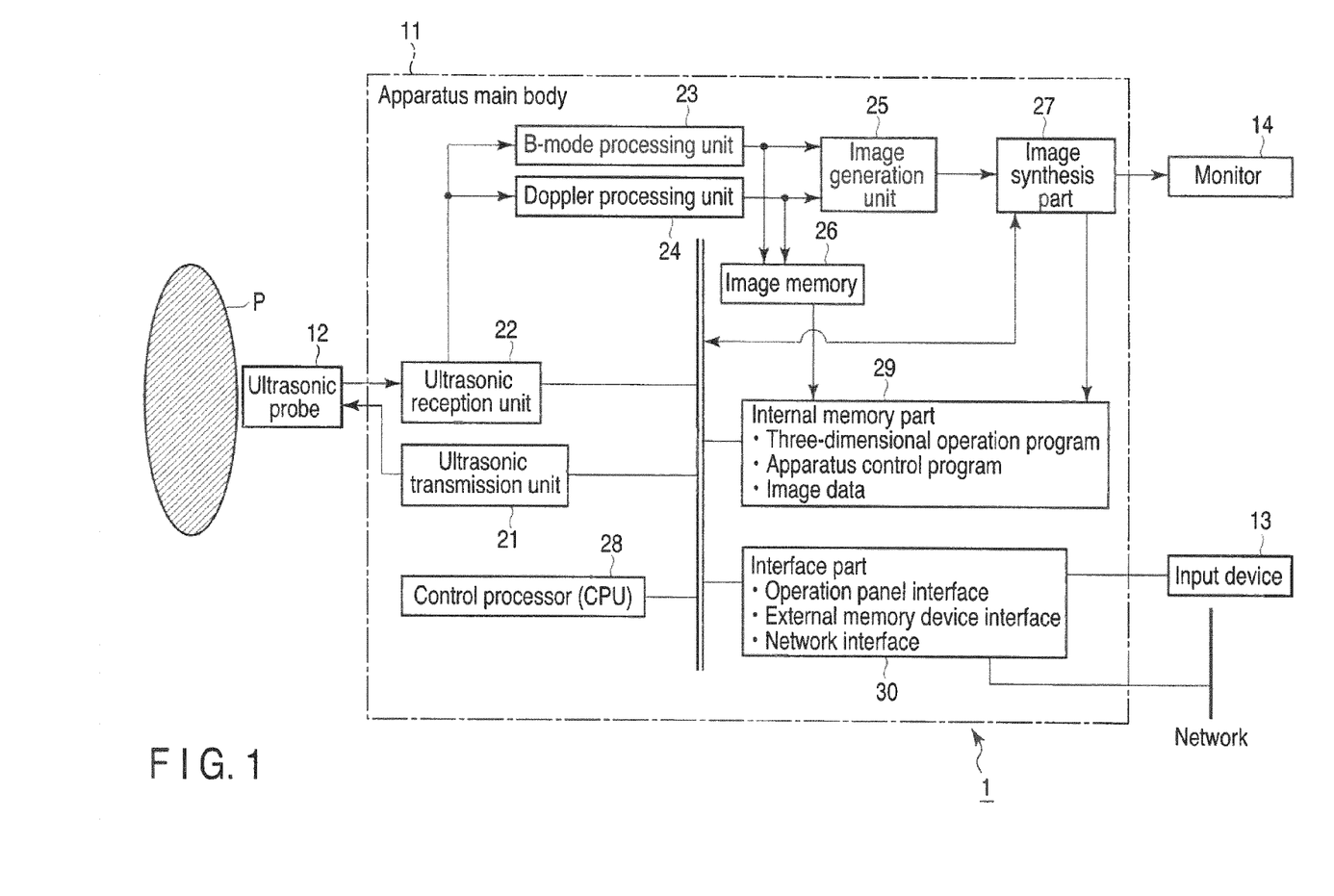
FIG. 1 is a block diagram illustrating a configuration of an ultrasonic diagnostic apparatus according to a first embodiment of the present invention.

FIG. 1 is a block diagram illustrating a configuration of an ultrasonic diagnostic apparatus 1 according to a first embodiment. As shown in FIG. 1, the ultrasonic diagnostic apparatus 1 comprises an ultrasonic probe 12, an apparatus main body 11, an input device 13, and a monitor 14.

The ultrasonic probe 12 generates ultrasound based on a driving signal from an ultrasonic transmission unit 21, and comprises a plurality of piezoelectric vibrators for converting a reflection wave from a test body into an electrical signal, a matching layer provided in the piezoelectric vibrator, and a packing material for preventing propagation of ultrasound from the piezoelectric vibrator to the rear side, for example. When ultrasound is transmitted to a test body P from the ultrasonic probe 12, the transmitted ultrasound is reflected off a discontinuous surface of an acoustic impedance of body tissue in turn, and received by the ultrasonic probe 12 as an echo signal. The amplitude of the echo signal depends on differences in acoustic impedance in the discontinuous surface, off which the reflection occurs. Further, an echo received when a transmitted ultrasonic pulse is reflected off the surface of the moving bloodstream or heart wall depends on velocity components of the moving body in the ultrasonic transmission direction by the Doppler effect, and receives a frequency shift.

The apparatus main body 11 comprises the ultrasonic transmission unit 21, an ultrasonic reception unit 22, a B-mode processing unit 23, a Doppler processing unit 24, an image generation unit 25, an image memory 26, an image synthesis part 27, a control processor (CPU) 28, an internal memory part 29, and an interface part 30. Hereinafter, functions of individual structural elements will be described.

The ultrasonic transmission unit 21 includes a trigger generating circuit, a delay circuit, and a pulser circuit, not shown. The pulser circuit repeatedly generates a rate pulse for forming transmission ultrasound at a predetermined rate frequency of fr Hz (period: 1/fr second). In the delay circuit, a delay time required to make ultrasonic waves converge into a beam in each channel and determine transmission directivity is given to each rate pulse. The trigger generating circuit applies a driving pulse to the ultrasonic probe 12 in a timing based on the rate pulse.

The ultrasonic transmission unit 21 has a function of instantly changing transmission frequencies, transmission drive voltages, and so forth, in order to perform a predetermined scan sequence according to instructions from the control processor 28. In particular, the change in transmission drive voltage is provided by an oscillator circuit of a linear amplifier type capable of switching the value instantly, or by a mechanism of switching a plurality of power supply units electrically.

The ultrasonic reception unit 22 includes, for example, an amplifier circuit, an analog-to-digital converter, and an adder, not shown. The amplifier circuit amplifies an echo signal captured through the ultrasonic probe 12 in each channel. The analog-to-digital converter supplies the amplified echo signal with a delay time required to determine reception directivity, and then the adder performs an adding process. This addition emphasizes reflection components from a direction according to the reception directivity of the echo signal, and the reception directivity and the transmission directivity form a general beam for ultrasonic transmission and reception.

The B-mode processing unit 23 receives an echo signal from the ultrasonic reception unit 22, subjects the echo signal to logarithmic amplification and an envelope detection process, and generates data whose signal intensity is expressed by brightness. This data is transmitted to the image generation unit 25, and displayed as a B-mode image, in which intensity of a reflected wave is expressed by brightness, on the monitor 14.

The Doppler processing unit 24 performs a frequency analysis for velocity information on the echo signal received from the ultrasonic reception unit 22, extracts echo components of the bloodstream, tissue, and a contrast agent by the Doppler effect, and obtains bloodstream information such as average velocity, dispersion, and power with respect to many points.

In general, the image generation unit 25 converts (scan-converts) a scanning line signal string of an ultrasonic scan into a scanning line signal string of a general video format as represented by television, for example, and generates an ultrasonic diagnostic image as a display image.

Further, the image generation unit 25 performs various kinds of image processing other than scan conversion. That is, the image generation unit 25 performs a scheme (smoothing process) of regenerating a brightness maximum image using a plurality of scan-converted image frames, and a scheme (difference operation) using a difference between images, for example, as well as the microstructure extraction process, which will be described later. Data before entering into the image generation unit 25 is sometimes referred to as "raw data".

The image memory (scene memory) 26 is a memory for storing an ultrasonic image corresponding to a plurality of frames immediately before freeze. By performing continuous display (scene display) of the ultrasonic image stored in the image memory 26, an ultrasonic moving image can also be displayed.

The image synthesis part 27 synthesizes the ultrasonic image received from the image generation unit 25 with character information and scales, for example, of various kinds of parameters, and outputs it as a video signal on the monitor 14.

The control processor 28 functions as an information processing device (computer), and controls operations of the ultrasonic diagnostic apparatus main body. The control processor 28 reads an exclusive program for implementing a microstructure extraction function and a control program for performing predetermined image generation and display, for example, from the internal memory part 29, develops them on a memory owned by itself, and performs operations or control of various processes.

The internal memory part 29 stores a predetermined scan sequence, an exclusive program for realizing a microstructure extraction function according to each embodiment, a control program for performing an image generation and display process, diagnosis information (patient IDs, views by doctors, and so forth), a diagnosis protocol, transmission and reception conditions, a CFAR process control program, a body mark generation program, and other groups of data. Further, the internal memory part 29 is also used for storing images in the image memory 26 as necessary. The data in the internal memory part 29 can also be transferred to an external peripheral device via the interface part 30.

The interface part 30 is an interface regarding the input device 13, a network, and a new external storage device (not shown). Data such as an ultrasonic image or an analysis result obtained by the device can be transferred to another device through a network by the interface part 30.

The input device 13 is connected to the apparatus main body 11, and includes various switches, buttons, a trackball, a mouse, and a keyboard for capturing various instructions, conditions, setting instructions for a region of interest (ROI), and various kinds of image quality condition setting instructions from the operator into the apparatus main body 11. For example, if the operator operates an END button or a FREEZE button of the input device 13, transmission and reception of ultrasound is finished, and the ultrasonic diagnostic apparatus is set to a suspension state.

The monitor 14 displays morphologic information (B-mode image) and bloodstream information (average velocity image, distribution image, power image, and so forth) in a living body, and a combination thereof, as an image, based on a video signal from the image generation unit 25.

A position detection device 15 can also be provided in the ultrasonic diagnostic apparatus 1 as necessary. The position detection device 15 detects information about the position of the ultrasonic probe 12 with respect to a photography object (that is, the area to be diagnosed). The information about the position of the ultrasonic probe 12 refers to information for specifying absolute positional information and relative positional information of the ultrasonic probe 12, positional information before movement and movement velocity and time of the ultrasonic probe 12, and the position of the ultrasonic probe 12 in other scanning.

Figure 2:
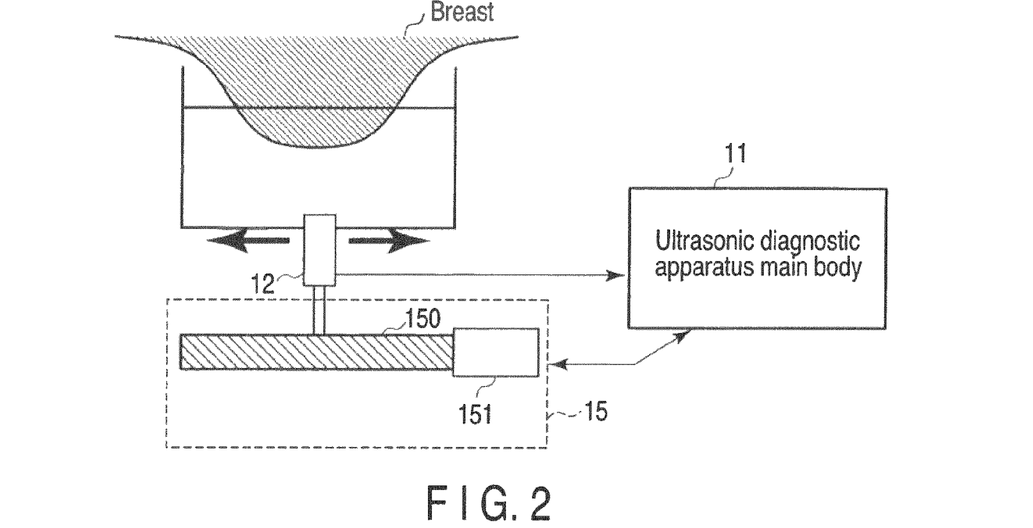
FIG. 2 illustrates an example of a position detection device.

FIG. 2 illustrates an example of the position detection device 15. As shown in FIG. 2, the position detection device 15 has a movable stage 150 and a drive 151. On the movable stage 150, the ultrasonic probe 12 can be provided through an exclusive adapter. The drive 151 moves the provided ultrasonic probe 12 along the movable stage 150 based on control from the control processor 28. Further, the drive 151 has a rotary encoder inside, for example, detects the position of the ultrasonic probe 12 on the movable stage 150, and transmits the detected result to the control processor 28 one by one.

In order to acquire an ultrasonic image, the breast, which is a diagnosis target, is placed in a predetermined position in a state of being immersed in a water tank 17, and is fixed so as not to move during the test. Further, the ultrasonic probe 12 and the position detection device 15 are placed at the bottom surface side of the water tank 17. The control processor 28 controls the drive 151 so that the ultrasonic probe 12 moves at a predetermined rate and simultaneously performs an ultrasonic transmission and reception process, and executes self-run ultrasonic scanning. An image from the ultrasonic probe 12 is sent to the apparatus main body 11. Further, positional information acquired by the drive 151 is used in real time for information generation regarding an ultrasonic probe position, which will be described later, and written and managed as auxiliary information in each frame.

Hereinafter, a microstructure extraction process, which is one of the main features of the ultrasonic diagnostic apparatus and program according to the first embodiment, will be described in detail.

When a bright point which is considered as a minute structure (hereinafter simply referred to as bright point) is observed in an ultrasonic tomogram (B-mode image), it is difficult to determine whether the minute structure is actually a structure such as a microcalcification or a part of a tissue structure such as the mammary gland. In particular, it is difficult to diagnose from only one still image.

However, the two are different in the following respects, for example.

(Difference 1) A composition of a microcalcification should be higher in hardness than body tissue, and in principle should receive bigger ultrasonic reflection signals. The research results by the inventors show that the signal level of the bright point corresponding to the structure formed of microcalcifications is slightly higher than the maximum value of the signal level of a neighboring speckle pattern. When the difference is displayed as brightness on the monitor, however, it is difficult to determine the difference in signal level by the eye.

(Difference 2) A structure formed of microcalcifications is a scattered microstructure. On the other hand, living body tissue such as the mammary gland is a continuous structure with a configuration which is three-dimensionally continuous in a predetermined range. Essentially, the two are greatly different in terms of form of spatial distribution. Accordingly, by considering the three-dimensional continuity in the depth direction, difference between the two can be determined.

Focusing the above-described point, the present embodiment distinguishes between the two based on minute differences in brightness, and forms of spatial distribution in diagnosis of the breast, the liver, the pancreas, or the like, and thereby generating an image (microstructure-extracted image) in which a microstructure is positively extracted.

The target of the microstructure extraction process in the first embodiment is image group data. The image group data refers to volume data having a plurality of two-dimensional images or data (not necessarily complete volume data) formed of a plurality of two-dimensional images.

In the first embodiment, in order to provide concrete descriptions, a microstructure extraction process using image group data as volume data will be described. The image group data can be acquired by, for example, photography using a device capable of self-run scanning as show in FIG. 2, or by photography using an ultrasonic probe (provided with a position sensor as necessary) in which ultrasonic vibration elements are arranged one-dimensionally and manually acquiring a plurality of cross-sections.

Figure 3:
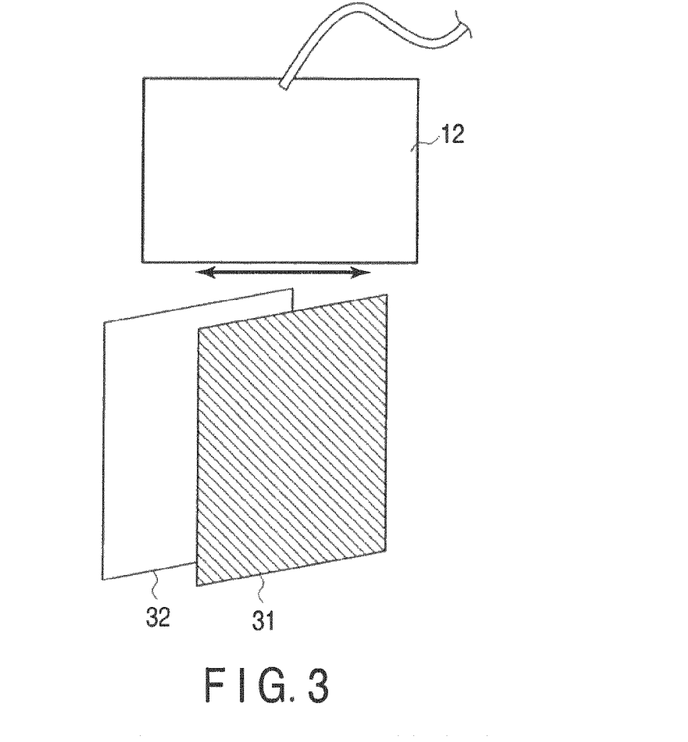
FIG. 3 illustrates a microstructure extraction process.

FIG. 3 illustrates a microstructure extraction process. As shown in FIG. 3, a target image 31 and a reference image 32 are selected from a plurality of two-dimensional images included in the image group data. The target image 31 is one of images which are targets of the microstructure extraction process, and is a tomogram (including a tomogram subjected to a process such as time smoothing) immediately under the ultrasonic probe 12. The reference image 32 is another tomogram in a position spatially different from the target image 31 (at a distance of k frames from the target image, for example), and is used for the microstructure extraction process. More specifically, the reference image 32 is an image of a preceding frame of the target image 31, and is an image stored in the image memory 26. These images are desirably vertical sections with respect to the main body of the ultrasonic probe, as in the case of the B-mode diagnosis.

Figure 4A:
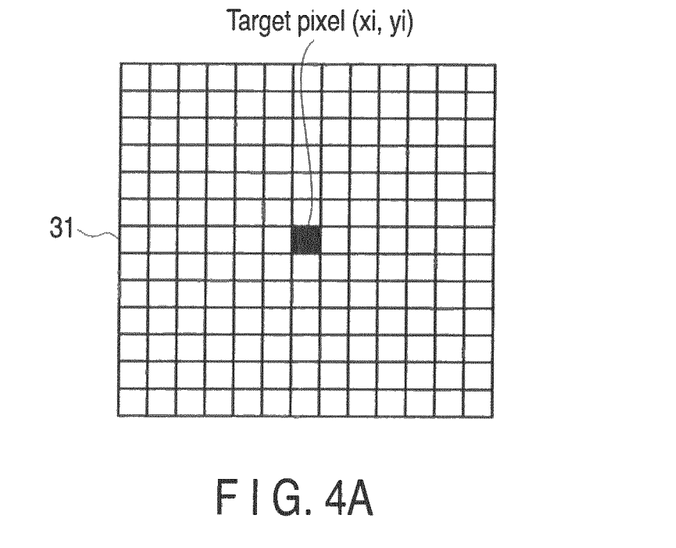
FIG. 4A is a schematic view of a target image.
Figure 4B:
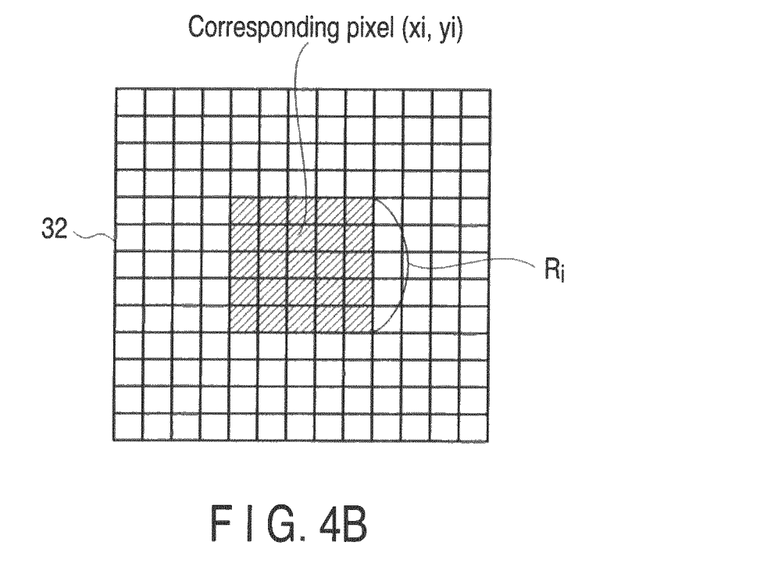
FIG. 4B is a schematic view of a reference image.

FIG. 4A is a schematic view of the target image. FIG. 4B is a schematic view of the reference image. In the microstructure extraction process, a differential image is generated by subtracting the reference image from the target image. In this process, a representative value of pixels present in a reference region Ri set on the reference image is determined with respect to each pixel (xi, yi) (which will be referred to as a target pixel) on the target image, and the representative value is subtracted from the value of the target pixel (xi, yi).

The reference region refers to a region set on the reference image in an arbitrary size such that coordinates on the reference image include the same pixel (corresponding pixel) as the target pixel. Any value representing characteristics of the reference region Ri may be used as the representative value of the reference region Ri. For example, the representative values may include the maximum value, the average value, and the median value. In the first embodiment, the maximum value is adopted as the representative value. Generation of the differential image can be expressed by the following formula (1):

$$Qi(xi, yi) = Pi(xi, yi) - \mathrm{MAX}[P_{i-k}(xi+m, yi+n)] \qquad (1)$$

where Qi (xi, yi) denotes the value of each pixel of the differential image, Pi (xi, yi) denotes the value of the target pixel on the target image, $P_{i-k}$ (xi, yi) denotes the value of each pixel on the reference image in a position spatially corresponding to Pi (xi, yi), $P_{i-k}$ (xi+m, yi+n) denotes the value of each pixel in the reference region Ri, m and n denote an arbitrary values specifying the size of the reference region, and MAXD denotes the operation of selecting the maximum value from [ ]. Accordingly, FIG. 4B exemplifies a reference region Ri formed of ±2 pixels both in the x-axis and the y-axis directions, i.e., of 25 pixels in total. In this subtraction process, all the negative results are desirably assumed to be zero (brightness value=black).

The differential image generated by the microstructure extraction process in the first embodiment removes continuous structures and random speckle pattern, and therefore suitably visualizes microstructures. This is based on the following reasons.

That is, a continuous structure remaining on a two-dimensional ultrasonic image forming image group data is a structure larger than a microstructure formed by microcalcification, and should have continuity in the depth direction. When one point in an ultrasonic tomogram is focused from this point of view, a continuous structure should show gradual changes in signal intensity (image brightness) (a) as shown in FIG. 5, for example.

Figure 5:
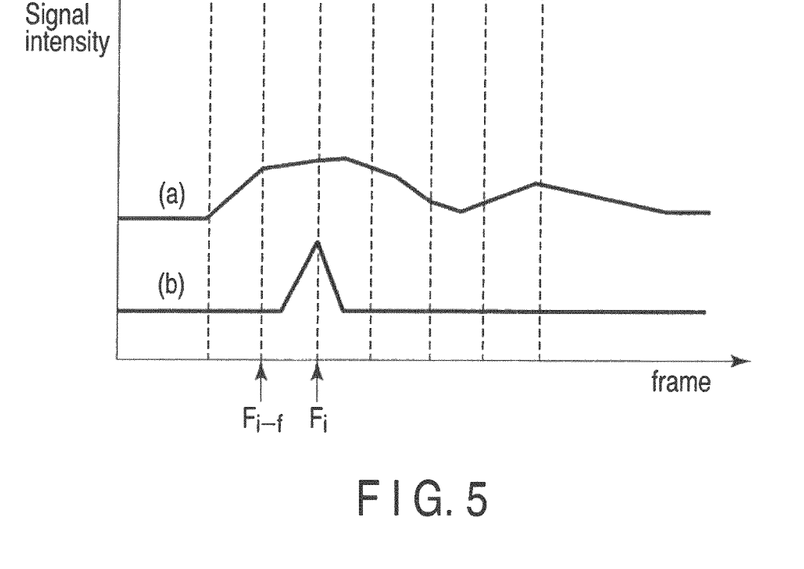
FIG. 5 illustrates an example of pixel-by-pixel change in signal intensity (image brightness).

A microstructure, on the other hand, should be included only in a specific image, as shown in signal intensity (b) of FIG. 5. Accordingly, when a differential image is generated from continuous or adjacent frame images (by subtracting an image Fi-f [reference image] from an image Fi [target image], for example), only discontinuously present microstructures (such as microcalcificied portions) can be extracted from the differential image.

Hereinafter, display forms of the microstructure-extracted image obtained by the microstructure extraction process will be described. The display forms which will be described in the embodiments may be used alone or in combination.

(Example Display Form 1)

Figure 6:
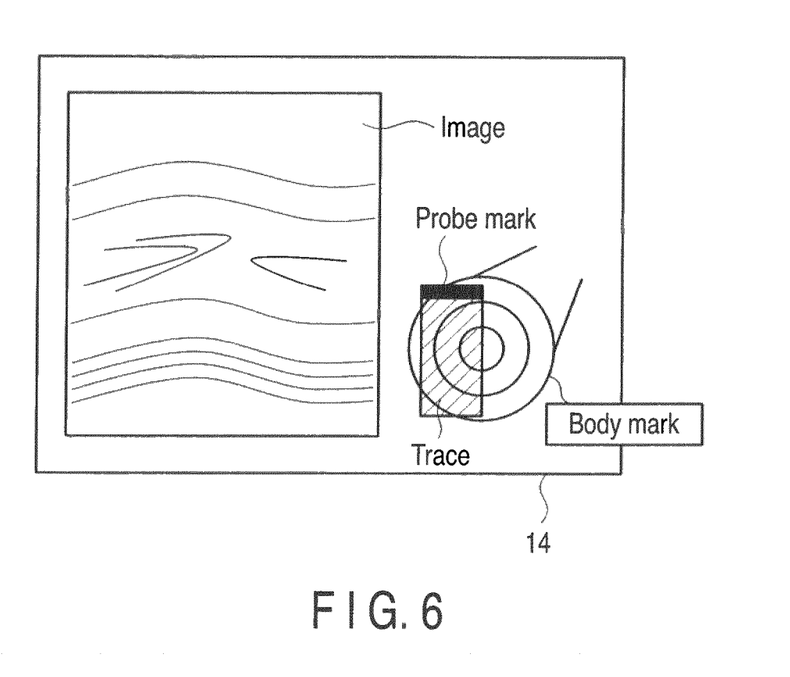
FIG. 6 illustrates an example of a display form of a microstructure extraction image.

In an example display form 1, a differential image as a microstructure-extracted image is displayed together with information indicating the position of the ultrasonic probe at the time of acquisition of the target image used for generation of the differential image. Any information satisfying that purpose may be used as the information indicating the position of the ultrasonic probe. A typical example is shown in the schematic view of the ultrasonic probe 12 set on a body mark, as shown in FIG. 6.

Such information indicating the position of the ultrasonic probe may be generated based on information detected by the position detection device 15 shown in FIG. 2, for example. In the case of the body mark shown in FIG. 6, the image synthesis part 27 generates a body mark indicating the position of the ultrasonic probe according to control from the control processor 28, synthesizes the body mark with a differential image, and transmits it to the monitor 14. Thereby, the differential image can be displayed together with the information indicating the position of the ultrasonic probe in the form shown in FIG. 6. As necessary, a scanning range or an already displayed region of the ultrasonic probe 12 may be displayed as "trace" on the body mark using color coding, based on all the positional information of the ultrasonic probe of a two-dimensional image forming the image group data.

(Example Display Form 2)

In an example display form 2, information about microstructures between image frames is subjected to an MIP process, and thereby displayed as a microstructure-extracted image.

Figure 7:
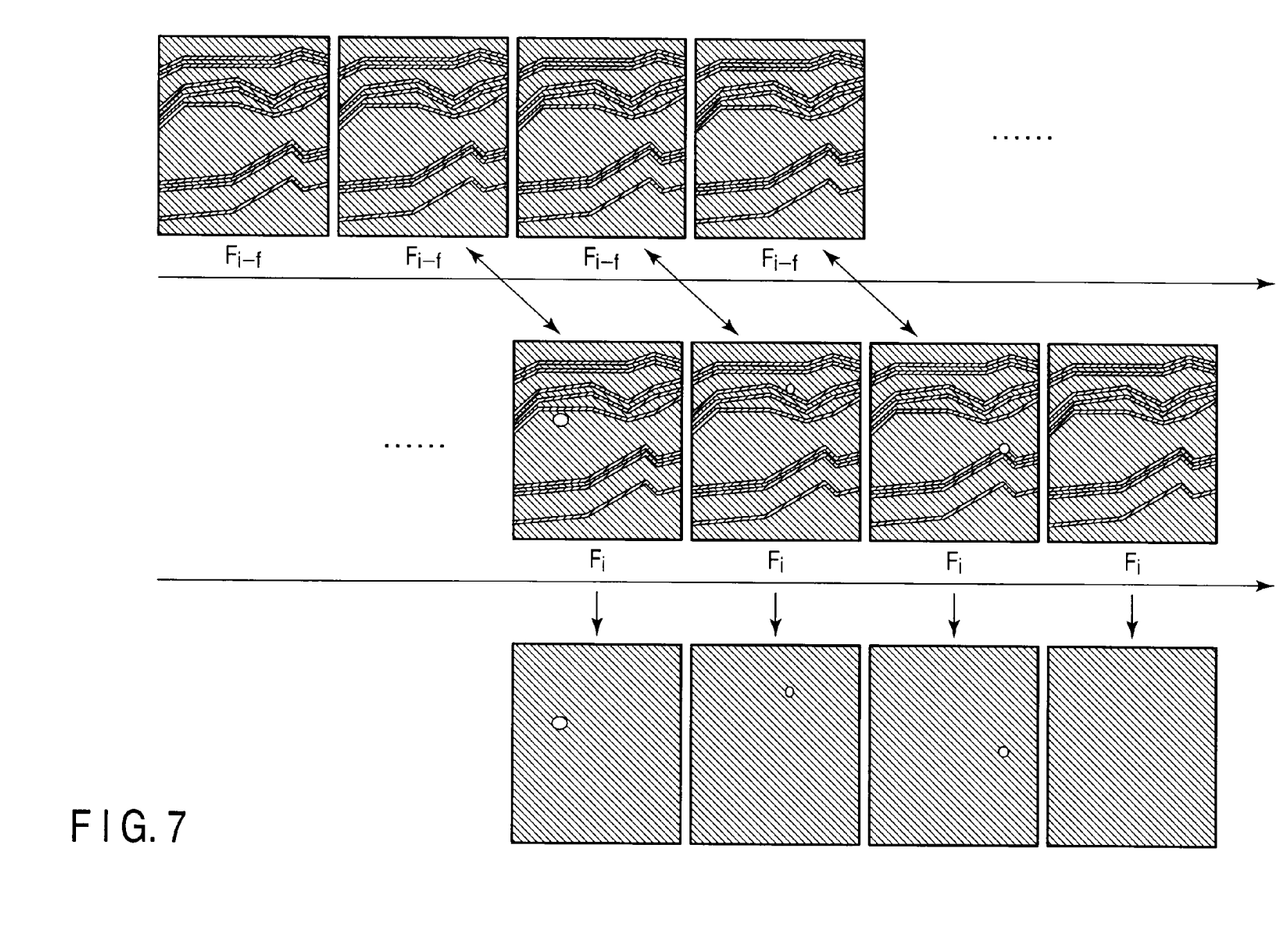
FIG. 7 illustrates another example of a display form of a microstructure extraction image.

First, the above-described microstructure extraction process is performed. That is, as shown in FIG. 7, a differential image (a differential image corresponding to the image group data, for example) of each of a plurality of image frames is generated by a process (process expressed by the formula (1), for example) of subtracting a reference image Fi_f (equivalent to the reference image 32) of each of the previously acquired and already stored image frames from a target image Fi (equivalent to the target image 31) of each of the image frames being photographed, with respect to each of the image frames. Then, the obtained differential images of a plurality of image frames are subjected to a process by the MIP method, and the resultant MIP image is displayed as a microstructure-extracted image. Thereby, information about microstructures included in a plurality of differential images can be squeezed into one MIP image. By using the MIP image as attached data for electronic charts, for example, it is possible to reduce the management data in size. The MIP is an abbreviation for a maximum intensity projection. In principle, the MIP is a method of performing a projection process from an arbitrary viewpoint with respect to three-dimensionally constructed data, and displaying the maximum value in the projection path on the plane of projection.

(Example Display Form 3)

In an example display form 3, first, a differential image having certain reliability is extracted from image group data using quantitative analysis. Then, the extracted differential image is subjected to the MIP process, as in the above-described case (example display form 2).

That is, a brightness curve is generated with respect to each pixel of a differential image corresponding to image group data, and an amount of change in time and a standard deviation thereof in a certain period (an interval between frames, for example) are calculated using the brightness curve. A pixel corresponding to the standard deviation (a standard deviation indicating a value greater than a predetermined threshold, for example) indicating a remarkably different value among the obtained results is most likely a pixel corresponding to a microstructure. Accordingly, after extracting a differential image having a pixel corresponding to the standard deviation indicating such a remarkably different value, a plurality of images extracted as differential images having the pixel corresponding to the standard deviation indicating the remarkably different value are subjected to a process by the MIP method. By performing such a processing step, extraction precision of microstructures can be improved.

(Example Display Form 4)

In a display form 4, a B-mode image prior to the microstructure extraction process, a microstructure-extracted image, and an MIP image obtained by an MIP process using a differential image, is displayed in the form of superimpose display, dual display, or triplex display. In the case of the superimpose display, it is possible to distinguish between a B-mode image prior to removal of a speckle pattern and a new image after the removal by superimposing them by changing the respective basic colors. Further, in parallel display such as dual display, in each display form in which different types of images are simultaneously displayed, a cursor is arranged in the same corresponding position in each image. Accordingly, the observer such as a doctor can make a microstructure-extracted image displayed in a desired display form and in desired timing according to the purpose, and specify and observe microstructures quickly and easily based on a plurality of kinds of images.

Figure 8:
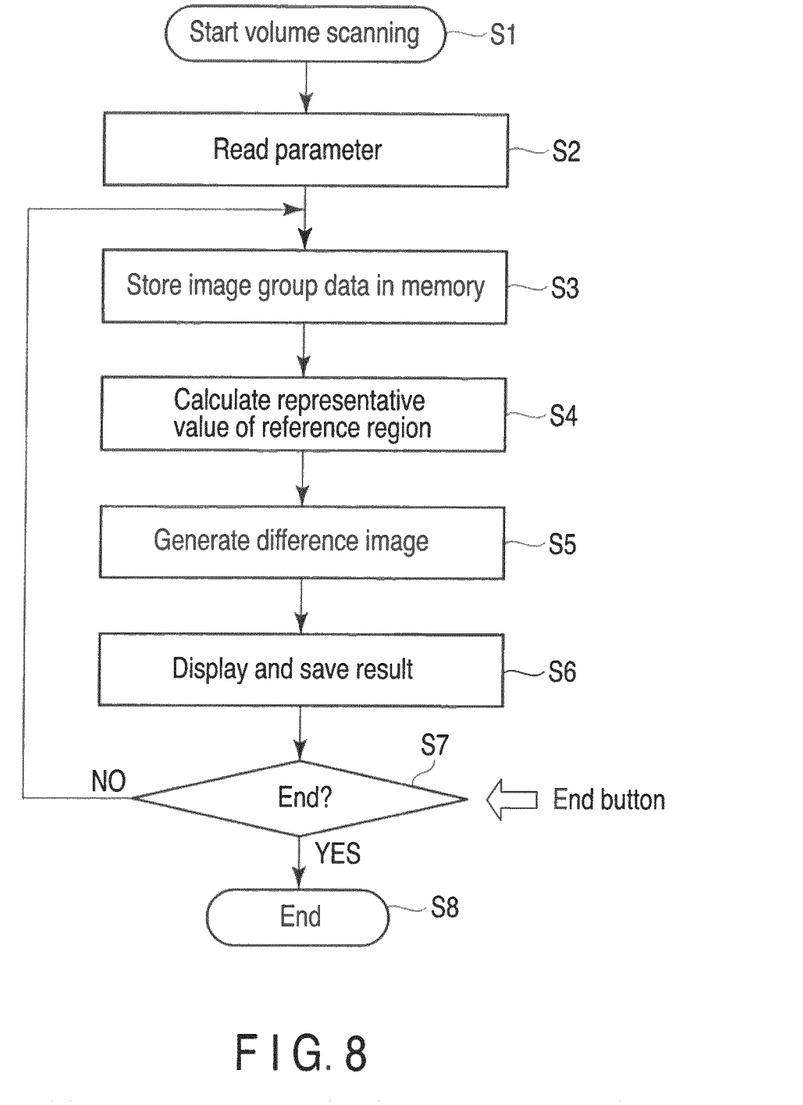
FIG. 8 is a flowchart illustrating a microstructure extraction process according to the first embodiment of the present invention.

Hereinafter, the microstructure extraction process by the ultrasonic diagnostic apparatus and program according to the first embodiment will be described with reference to the flowchart shown in FIG. 8. In order to provide concrete descriptions, in the example shown in FIG. 8, the display form according to the display form example 1 will be adopted. Upon receipt of an instruction to shift to the microstructure extraction process concurrently with the start of volume scanning, a group of necessary parameters is read (Steps S1, S2), as shown in FIG. 8. The group of parameters necessary for the microstructure extraction process refers to the number of reference images, the distance from a target image, a region of a smoothing process (maximum value operation).

Then, image group data regarding the breast is acquired by volume scanning using a predetermined scheme, and is stored in a memory (Step S3). After that, the image generation unit 25 calculates a representative value of a reference region with respect to each reference image (Step S4), and performs the above-described microstructure extraction process using the calculated representative value to generate a plurality of difference images corresponding to the image group data (Step S5). The acquired difference image is displayed together with a body mark indicating positional information of the ultrasonic probe on the monitor 14, for example, and is saved automatically (Step S6).

After that, the diagnosis device repeatedly performs the microstructure extraction process until an image freezes or an instruction to finish the video mode of the present invention is provided.

By programming the above-described series of processes using the ultrasonic diagnostic apparatus according to the first embodiment, or by reading the program into a storage medium after the programming, it becomes easy to sell and distribute the series of processes as a single software product independent from medical image diagnosis apparatuses, and the technique according to the first embodiment can be used on other hardware devices too.

As described above, according to the first embodiment, it is possible to accurately distinguish between continuous structures such as the mammary gland and microstructures such as microcalcified portions, and provide an ultrasonic diagnostic apparatus and program capable of obtaining a desired microstructure-extracted image in real time, using a conventional 1D ultrasonic probe as an ultrasonic probe.

That is, according to the ultrasonic diagnostic apparatus and program of the first embodiment, microstructures can be extracted in real time by using difference in spatiality (spatial (3D) information) between continuous structures and microstructures using a 1D ultrasonic probe. In other words, by use of a widely prevalent 1D ultrasonic probe, which does not lose real-time properties, a pseudo-positive reaction, which cannot be sufficiently reduced by signal processing only within a tomogram.

More specifically, according to the ultrasonic diagnostic apparatus of the first embodiment, discontinuously present microstructures are extracted in real time using information regarding the direction (depth direction) substantially crossing the image in diagnoses of the breast, the liver, pancreas, and so forth, using a conventional 1D ultrasonic probe (including a 1.5D ultrasonic probe) as an ultrasonic probe. The maximum value smoothing in the microstructure extraction process enables effective removal of residuals due to variation in speckle pattern and deviation in position in the cross-sectional direction of the structure. A mere difference calculation between a target image and a reference image cannot completely remove residuals due to variation in speckle pattern and deviation in position in the cross-sectional direction of the structure.

Figure 9A:
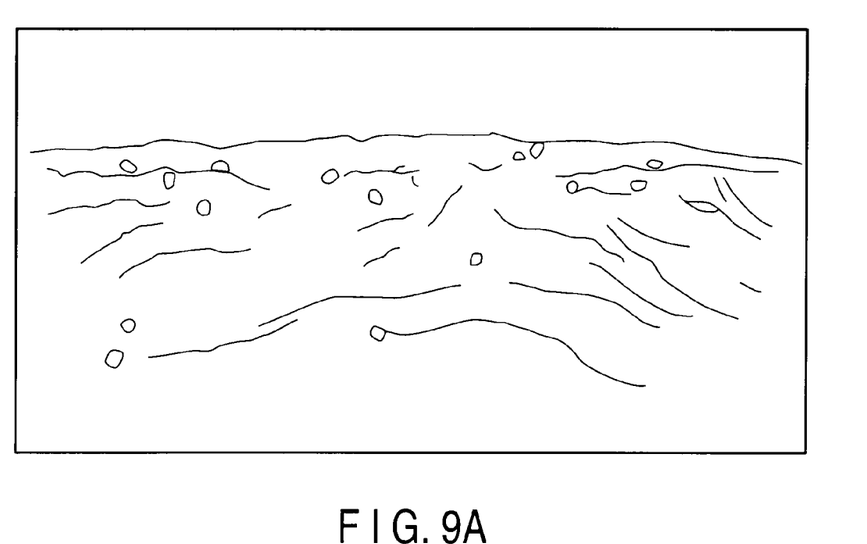
FIG. 9A illustrates a normal B-mode image.
Figure 9B:
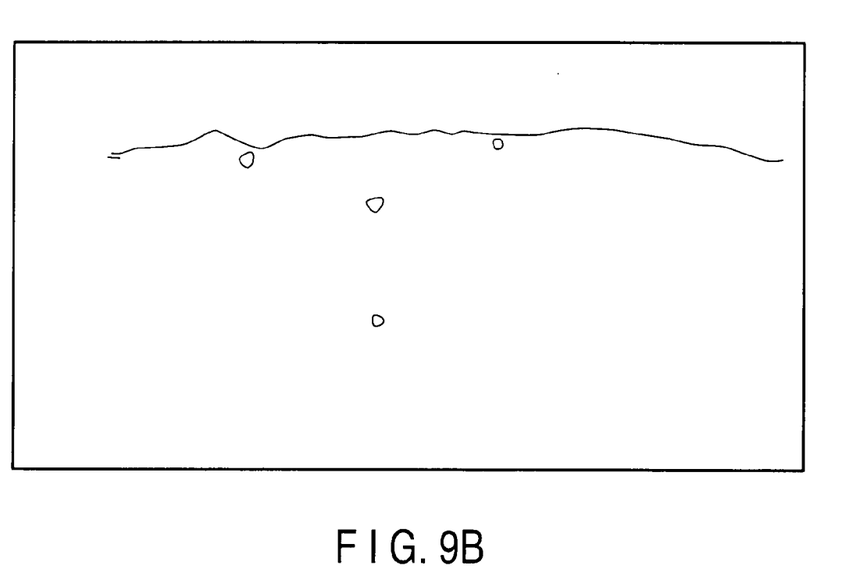
FIG. 9B illustrates a microstructure extraction image.

FIG. 9A illustrates a normal B-mode image, and FIG. 9B illustrates a microstructure-extracted image.

When the two are compared, the normal B-mode image shown in FIG. 9A visualizes some portions of tissue as well as microcalcified parts, and many dotted high-brightness portions are scattered. This makes it difficult to specify which dot corresponds to the microcalcificied part by the naked eye.

The microstructure-extracted image shown in FIG. 9B, on the other hand, extracts and visualizes only microcalcified parts as dotted high-brightness portions. It is therefore possible to distinguish between continuous structures which are continuously distributed three-dimensionally, and microstructures which are topically scattered, and generate and display in real time a microstructure-extracted image on which microstructures are extracted. A doctor, for example, can detect, in a short time, microstructures which are difficult to be distinguished from a speckle pattern and appear only in a specific cross-sectional image by observing an image on which microstructures are extracted and displayed.

In the ultrasonic diagnostic apparatus according to the first embodiment, the size of the frame and the reference region used as a reference image for use in the microstructure extraction process can be arbitrarily selected. Accordingly, by setting the size of the frame or the reference region used as the reference image depending on the purpose of test or individual difference, preferable visualization of microstructures can be performed according to individual situations.

Further, in the ultrasonic diagnostic apparatus according to the first embodiment, various kinds of display forms can be adopted, as will be exemplified below. That is, adoptable display forms include displaying a microstructure-extracted image together with a body mark in which the position of the ultrasonic probe and the scanning range at the time of acquisition of the target image are set, displaying an MIP image generated using a differential image obtained by a microstructure extraction process in a predetermined form, or displaying an image before and after the microstructure extraction in a predetermined form.

Accordingly, a doctor, for example, can detect in real time microstructures, which are difficult to be distinguished from a speckle pattern and appear only in a specific cross-sectional image, by the naked eye by observing microstructure-extracted images in a desired display form or by comparing microstructure-extracted images in various kinds of display forms.

Second Embodiment

Hereinafter, an ultrasonic diagnostic apparatus and program according to the second embodiment of the present invention will be described. In order to avoid overlapping descriptions with the first embodiment, only differences from the first embodiment will be described.

Figure 10:
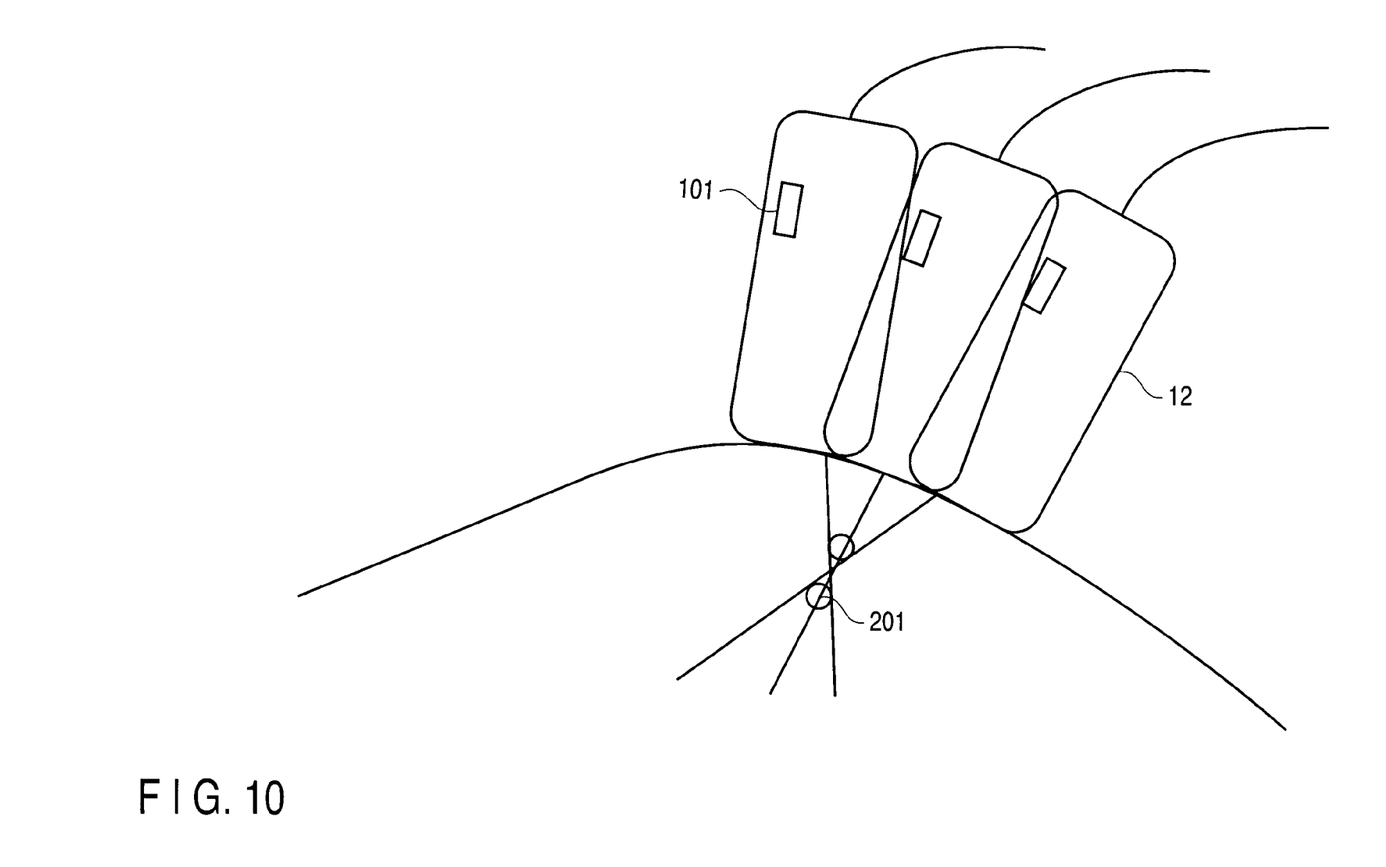
FIG. 10 illustrates an ultrasonic probe of an ultrasonic diagnostic apparatus according to a second embodiment of present invention.

In the ultrasonic diagnostic apparatus according to the second embodiment, as shown in FIG. 10, a microposition sensor 101 is attached to or built into the ultrasonic probe 12. The microposition sensor 101 detects an amount of movement in the position of the ultrasonic probe 12, and based on frame rates, etc., calculates a tomogram frame interval appropriate for extraction of a target microstructure 201. Based on the tomogram frame interval thus calculated, the microstructure extraction process as described in the first embodiment is performed.

In the second embodiment, when stop of movement of the ultrasonic probe 12 is detected by the microposition sensor 101, the following step is performed.

(Process Example 1, at the Time of Stop of the Ultrasonic Probe)

When stop of movement of the ultrasonic probe 12 is detected by the microposition sensor 101, the process is changed to a process (process which does not use a plurality of tomograms acquired by the ultrasonic probe 12 in the same position) which uses only the tomogram immediately under the ultrasonic probe 12 at that point in time.

(Process Example 2 at the Time of Stop of the Ultrasonic Probe)

When stop of movement of the ultrasonic probe 12 is detected by the microposition sensor 101, the tomogram acquired during the stop period is deleted (or is not used), and when movement of the ultrasonic probe 12 is resumed, the above-described process is performed using the tomogram immediately before the stop period.

As described above, according to the second embodiment, similar advantageous effects as those of the ultrasonic diagnostic apparatus and program according to the first embodiment can be obtained, and an ultrasonic diagnostic apparatus and program capable of performing a microstructure extraction process with higher precision can be provided.

Third Embodiment

Hereinafter, an ultrasonic diagnostic apparatus and program according to the third embodiment of the present invention will be described. In order to avoid overlapping descriptions with the first embodiment, only differences from the first embodiment will be described.

In the ultrasonic diagnostic apparatus according to the third embodiment, based on correlative information between tomograms, an amount of movement in position of the ultrasonic probe 12 or similarity between the tomograms is calculated, and a tomogram frame interval suitable for extraction of a target microstructure is calculated based on the calculated result. Based on the tomogram frame interval thus calculated, the microstructure extraction process as described in the first embodiment is performed.

(When the Amount of Movement of the Ultrasonic Probe is Calculated)

Based on the calculated frame rate, for example, of the ultrasonic probe 12, a tomogram frame interval suitable for extraction of a target microstructure is calculated. When stop of movement of the ultrasonic probe 12 is detected, a similar process as the process at the time of stop of movement of the ultrasonic probe 12 in the ultrasonic diagnostic apparatus according to the second embodiment is performed.

(When Similarity between Tomograms is Calculated)

Based on similarity between the calculated tomograms, a microstructure extraction process as described in the first embodiment is performed between a current frame and a frame which greatly varies from the current frame in similarity. When similarity is always high in more than a predetermined certain number of tomograms stored in the image memory 26, it is judged that movement of the ultrasonic probe 12 has stopped, and a process similar to the process at the time of stop of movement of the ultrasonic probe 12 in the ultrasonic diagnostic apparatus according to the second embodiment is performed.

As described above, according to the third embodiment, an ultrasonic diagnostic apparatus and program capable of obtaining advantageous effects similar to those of the ultrasonic diagnostic apparatus and program according to the first embodiment and performing a microstructure extraction process with higher precision can be provided.

The present invention has been described as above based on the first to third embodiments, but the present invention is not limited to the above-described embodiments, and various modifications and applications can of course be made within the scope of the invention.

Furthermore, the above-described embodiments include various stages of the invention, and various inventions can be extracted by appropriate combination of the structural elements disclosed therein. For example, when the problem stated in the description about the problems to be solved can be solved and the advantageous effects as those stated in the descriptions about the advantageous effects of the invention can be obtained even by deleting some of the structural elements from all the structural elements disclosed in the embodiments, the structures from which such constituent elements are deleted may be extracted as an invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus configured to ultrasonically scan a test body and acquire a tomogram, the apparatus comprising:
   an ultrasonic probe configured to transmit ultrasound to the test body and receive an echo signal from the test body;
   a position detector configured to detect a position of the ultrasonic probe at each of a plurality of timings;
   processing circuitry configured to generate a plurality of time series tomograms of the test body based on outputs from the ultrasonic probe, the time series tomograms corresponding to the plurality of timings, respectively;
   a memory configured to store the time series tomograms generated by the processing circuitry,
   wherein the processing circuitry is further configured to determine a frame interval based on an amount of movement calculated from positions detected by the position detector and a frame rate at which the time series tomograms are generated,
   select, from among the time series tomograms stored by the memory, a reference tomogram at the frame interval from a target tomogram included in the time series tomograms, the reference tomogram being generated prior to the target tomogram, and
   generate a microstructure-extracted image based on the reference tomogram and the target tomogram; and
   a display configured to display the microstructure-extracted image generated by the processing circuitry in a predetermined form.

2. The ultrasonic diagnostic apparatus according to claim 1, wherein
   the memory stores the tomograms generated by the processing circuitry in association with the detected position; and
   the processing circuitry is further configured to
      determine a reference region on the reference tomogram, determine a representative pixel value of the reference region, representing a characteristic of the reference region, and generate the microstructure-extracted image by subtraction using the reference region representative pixel value and a pixel value of each of pixels of the target tomogram.

3. The ultrasonic diagnostic apparatus according to claim 2, wherein the representative pixel value is any one of a maximum value, an average value, and a median value of a pixel value of each of pixels in the reference region.

4. The ultrasonic diagnostic apparatus according to claim 2, wherein the processing circuitry is further configured to generate a differential image by subtracting the representative pixel value from the pixel values of target pixels of the target tomogram, and extract the microstructure, based on a variation in a signal intensity of pixel values between pixels in the differential image.

5. The ultrasonic diagnostic apparatus according to claim 1, further comprising a drive configured to move the ultrasonic probe at a predetermined velocity.

6. The ultrasonic diagnostic apparatus according to claim 1, wherein the position detector is attached to or built into the ultrasonic probe.

7. An ultrasonic image acquiring method for ultrasonically scanning a test body and acquiring a tomogram, the method comprising:

transmitting ultrasound to the test body by an ultrasonic probe and receiving an echo signal from the test body;

detecting, by a position detector, a position of the ultrasonic probe at each of a plurality of timings;

generating a plurality of time series tomograms of the test body based on outputs from the ultrasonic probe, the time series tomograms corresponding to the plurality of timings, respectively;

storing the generated time series tomograms in a memory;

determining a frame interval based on an amount of movement calculated from positions detected by the position detector and a frame rate at which the time series tomograms are generated;

selecting, from among the time series tomograms stored by the memory, a reference tomogram at the frame interval from a target tomogram included in the time series tomograms, the reference tomogram being generated prior to the target tomogram;

generating a microstructure-extracted image based on the reference tomogram and the target tomogram; and displaying the microstructure-extracted image.

* * * * *